United States Patent
Weissman

[11] Patent Number: 5,785,525
[45] Date of Patent: Jul. 28, 1998

[54] DENTAL IMPLANT SYSTEM

[76] Inventor: Bernard Weissman, 225 E. 48th St., New York, N.Y. 10017

[21] Appl. No.: 649,410

[22] Filed: May 17, 1996

[51] Int. Cl.$^6$ ............................................. A61C 8/00
[52] U.S. Cl. ............................................ 433/174; 433/176
[58] Field of Search .............................. 433/173, 174, 433/175, 176, 201.1

[56] References Cited

U.S. PATENT DOCUMENTS

| | | | |
|---|---|---|---|
| 3,708,883 | 1/1973 | Flander | 433/174 |
| 3,934,347 | 1/1976 | Lash et al. | 433/201.1 |
| 4,624,673 | 11/1986 | Meyer | 433/173 |
| 4,626,214 | 12/1986 | Artal | 433/174 |
| 4,645,453 | 2/1987 | Niznick | 433/173 |
| 4,762,492 | 8/1988 | Nagai . | |
| 4,934,935 | 6/1990 | Edwards | 433/174 |
| 5,061,181 | 10/1991 | Niznick | 433/174 |
| 5,125,839 | 6/1992 | Ingber et al. | 433/173 |
| 5,205,746 | 4/1993 | Chanavaz . | |
| 5,246,369 | 9/1993 | Poulmaire | 433/174 |
| 5,246,370 | 9/1993 | Coatoam | 433/173 |
| 5,312,256 | 5/1994 | Scortecci | 433/174 |
| 5,427,527 | 6/1995 | Niznick et al. | 433/174 |
| 5,547,377 | 8/1996 | Daftary | 433/173 |
| 5,564,923 | 10/1996 | Grassi et al. | 433/173 |
| 5,564,924 | 10/1996 | Kwan | 433/173 |

FOREIGN PATENT DOCUMENTS

| | | | |
|---|---|---|---|
| 126624 | 11/1984 | European Pat. Off. | 433/174 |
| 1958338 | 11/1969 | Germany | 433/173 |
| 2176709 | 1/1987 | United Kingdom | 433/174 |

*Primary Examiner*—Ralph Lewis
*Attorney, Agent, or Firm*—Helfgott & Karas, PC

[57] ABSTRACT

An implant body has a non-round cross sectional shape, for example, ovoidal or rectangular. Lateral surfaces of the implant include threaded portions of a circular cylinder such that the implant, although non-round in cross section, can threadably engage a tapped circular opening in the jawbone leaving lateral spaces. Bone grows into the spaces between implant and the jawbone socket. The implant is shaped similarly to the root structure of a natural tooth and can be oriented, about its longitudinal axis, at any angle relative to the general curvature of the jawbone where the implant is seated. A more natural appearance of the mouth is achieved; prosthetic teeth may be positioned closer together without loss of strength between the implant and the jawbone. A non-round cross section of an implant opening receives an abutment post of corresponding cross section to prevent rotation of the abutment relative to the implant. A cemented connection prevents axial displacement between the abutment and implant. No screws are used in the prosthesis.

14 Claims, 2 Drawing Sheets

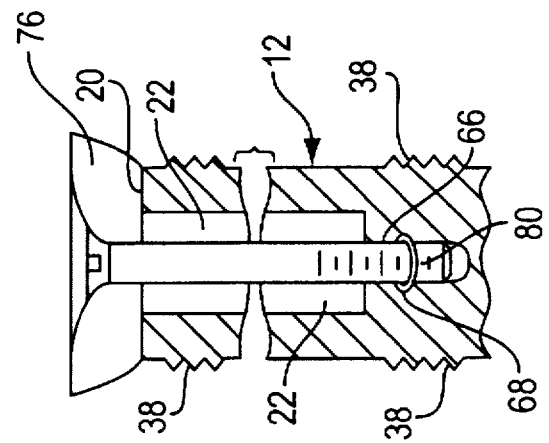
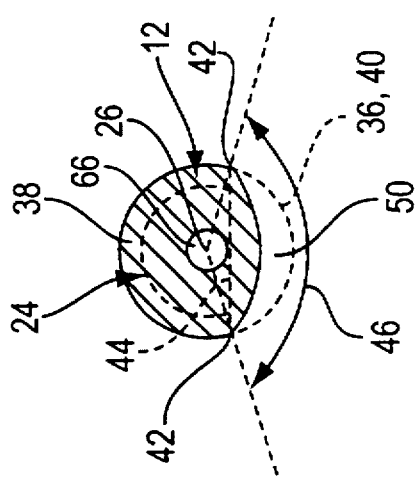

DENTAL IMPLANT SYSTEM

BACKGROUND OF THE INVENTION

This invention relates generally to a dental prosthesis and more particularly to a dental prosthesis that includes an implant in the bone of a person's jaw.

It is not uncommon, when it is desired or necessary to replace a missing tooth or teeth, that the gum is opened, a hole is drilled, and an implant is embedded in the bone structure beneath the gum. The earliest dental implants used for supporting missing teeth were cylindrical screws that were threaded into a prepared hole in the jawbone. An extended section protruded above the bone and soft tissue for attachment to and support of crowns and other restorations. The screw type implants were made of chrome-cobalt alloy or rust-free stainless steel in a variety of sizes and lengths. The protruded portion above the bone and soft tissues were of varying constructions and shapes. The opening in the jawbone was made with conventional spiral drills or with water cooled diamond coated high speed instruments. Additionally, loose mobile teeth were stabilized by similar screw forms placed in the canal of the loose tooth and driven through the tooth apex into the underlying bone.

After many years of using screw type implants, a new implant design was introduced to accommodate different locations and jaw sizes, especially, in narrow cross sections of the lower jawbone, and to provide greater stability and support. The new design, generically known as a blade-implant, had a rectangular form and was manufactured in various thicknesses and lengths with an array of indentations, deformations or perforations through its cross sections. The blade implants were made of various metal alloys and were initially cast by the lost wax process or milled from solid material in accordance with individual needs.

Blade implants were installed in longitudinally prepared troughs cut along the jawbone ridge to a desired depth. The implant was held frictionally in the bone after being gently hammered into place. After installation and suturing of the surgical site, a protruding buttress was prepared using known dental procedures for fitting a crown supporting single or multiple tooth replacements.

Both the early screw type and the later blade implants were loaded and put to use by allowing the patient to chew and function in a conventional manner immediately after installation of the implant. The blade implants, enjoyed a long period of use and considerable success. They were replaced as a preferred device when the presently popular titanium implants were developed.

These new implants have a substantial advantage over the prior art in that after implantation and over a period of time, the titanium becomes integral with the bone. The titanium or "submergible" implant is installed by the same mechanical techniques, and are frictionally held or threaded into the bone; they are allowed to heal (osseointegrate) before using them for normal chewing and biting functions.

Concurrently with introduction of the titanium implants some 25 years ago, a new and distinctive surgical installation protocol was developed using highly specialized drilling devices under careful observation and surgical installation procedures.

Lengthy investigations and studies related to the use of "submergible" titanium implants have since shown that when all clinical procedures are followed in accordance with tested methods, osseointegration will proceed. The bone remolds around the metal implants, thus providing strong anchorage and long term service as supports for missing teeth. Materials other than titanium and suitable for implants may exist or be developed with similar integration characteristics.

After the implant has integrated with the bone, a process which may take from 4 to 9 nine months depending upon the location in the jawbone, the gum above the implant is opened to expose the proximal end of the implant. An abutment attaches to the implant and a crown simulating a real tooth attaches to the abutment. Alternatively, the crown may attach directly to the proximal end of the integrated implant.

However, while the implant is firmly anchored to the jawbone, problems have arisen in providing suitable attachment between the implant and an abutment or between the implant and crown when no intermediate abutment is used. Frequently, an abutment is attached to a tapped hole axially formed in the implant using a screw that passes through the abutment or crown and engages the tapped hole. For preventing rotation of the prosthesis on the implant, the protruding proximal end of the implant requires a non-round shape that interlocks with a complementary shape on the abutment. A hexagonal shape is commonly used. Use of a screw that passes through the crown and engages a tapped hole in the implant is very common and such constructions are available from many manufacturers.

Following complete healing and osseointegration, the protruding abutment, which may be of different sizes with different angulations as in the prior art, is attached to the central inner thread of the submerged implant using a small screw. Another smaller screw may be used for attaching teeth (crown) upon the protruding buttress head.

Until now, these popular and widely used submerged implant fixtures with multiple screw connection techniques were tolerated in spite of knowledge that the implants often fail to function in retaining the prosthesis in proper position. This failure frequently occurs because screws of a small size, which might be used in wrist watch, are the anchors that must resist the known high levels of masticatory loads.

In using multiple titanium implants, because the jawbone is narrow, it has been necessary to place adjacent implants on wide-spaced center lines so that a strong web of bone separates adjacent implants. Thus, implants cannot be spaced as close together as would be desired in many instances. Also, there is a problem where an implant is desired between narrowly separated natural teeth. Drilling a hole in the jawbone between the natural teeth to permit insertion of an implant may leave no bony structure between the implant and the adjacent natural teeth, a weak construction.

Frequently, an implant is damaged during installation. In time, under the masticatory loads, this initial damage progresses to the degree that it is no longer possible to maintain the crown in its intended fixed position.

What is needed is a tooth implant that maintains the artificial crown in proper position over extended periods of use without reliance on screw thread techniques to maintain integrity. Also, closer placement of implants in the jawbone relative to adjacent implants and natural teeth is desirable.

SUMMARY OF THE INVENTION

Accordingly, it is an object of the invention to provide an improved dental implant system that osseointegrates with the jawbone and holds a crown in position over extended periods of time without usage of screw type devices between the implant and the crown.

Another object of the invention is to provide an improved dental implant system having an implant that is readily tapped into the bone without damage to the implant.

Yet another object of the invention is to provide an improved implant system that permits closer spacing to adjacent implants and natural teeth while providing a strong bone structure to support the implants.

A further object of the invention is to provide an improved dental implant system that is installed in the mouth of a person using procedures very similar to procedures now in use.

In the implant system in accordance with the invention, rounded shapes and features of prior art implants are replaced by non-round shapes. That is, the body of the implant, which is generally a circular cylinder with external threads in the prior art, is replaced with a non-round cross sectional shape, for example, ovoidal or rectangular. Lateral surfaces of the implant include portions of a circular cylinder having an axis that passes longitudinally through the implant. The cylindrical portions bear thread segments such that the implant, although non-round in cross section, can threadably engage a tapped circular opening in the jawbone. The circular opening is of the same diameter as the cylindrical portions on the lateral surface of the implant so that the implant may be threaded into the circular opening.

That is, over the length of the implant, there may be no continuous external threaded cylindrical surface that corresponds in full circumference to the cylindrical opening formed in the jawbone to receive the implant. Therefore, in early use, portions of the implant are spaced away from the cylindrical walls of the socket opening in the bone. Nevertheless, intervals of threaded engagement with the hole in the bone prevents wobble of the implant in the jawbone even though full contact does not exist between the implant and bone at the time of installation. Generally threaded portions on the implant that exceed 180° of arc as viewed along the longitudinal axis, maintain the implant in its desired position in the bone opening, without wobble. This is especially important near the proximal and distal ends of the implant.

Because the implant in accordance with the invention does not fully occupy the cylindrical hole formed in the jawbone, the implant may be shaped similarly to the root structure of the tooth that is missing and being replaced. For example, the distal end may be bifurcated to simulate such a tooth root, as necessary. The rectangular or ovoidal implant can be oriented, about its longitudinal axis, generally parallel with, at a right angle, or at any angle relative to the general curvature of the jawbone where the implant is seated.

The distal end of the implant may include a tip having self tapping threads that are co-axial with the cylindrical portions that threadably engage the bone opening. These distally located threads defining a tapered helix, tap into the bone at the bottom of the jawbone opening to further stabilize the implant in the jawbone immediately after installation.

As earlier studies have proven, the bone will grow into the spaces that are left between the titanium implant and the cylindrical opening or socket originally drilled into the jawbone to receive the implant. Thus, when a plurality of adjacent implants are required, the initial cylindrical socket holes can be drilled in the bone closer together than in the prior art. Similarly the socket can be drilled closer to natural teeth. The spaces left by the non-round contours of the implant body will ultimately fill with growth material and osseointegrate with the titanium implant. (Bone chips may be used to augment the healing process, as is known in the art). Thereby, a more natural appearance of the mouth may be achieved; prosthetic teeth may be positioned closer together without loss of strength between the implant and the jawbone.

A central opening extends longitudinally from the proximal end of the implant body toward the distal end. The opening is not round but corresponds at the proximal end to the cross section periphery of the implant itself. Thus, as viewed from the proximal end, a non-round, that is, a generally ovoidal or rectangular opening, is presented on the face of the implant. A key-hole shape may also be used. The central opening extends in its non-round cross section toward the distal end and terminates in a blind bottom short of the distal end.

In use, a crown connects to a core of an abutment which also includes a bayonet type post that is received in the central opening of the implant. The post is shaped in cross section to correspond with the non-round contours of the central opening, and is therefore received firmly with a preselected orientation, and held therein with cement.

The non-round cross section of the implant opening and the corresponding cross sections of the post prevent rotation of the core relative to the implant, while the cemented connection prevents axial displacement between the core and the implant.

In installing the implant in the prepared jawbone opening, the non-circular elongated opening in the implant allows for entry of a correspondingly shaped tool, similar to a conventional screw driver, that facilitates controlled threading of the implant into the structure. Danger of slippage between the implant and the driving tool during installation is virtually eliminated by the distinctly non-round shape of the opening. Damage to the implant is avoided.

In an alternative embodiment, an O-ring that is seated at the distal end of the central opening in the implant, receives the distal end of the post, such that the practitioner gets feedback, that is a "feel", that the post is properly seated in the implant at the final setting after the cement is applied.

The invention accordingly comprises the features of construction, combinations of elements, and arrangements of parts, which will be exemplified in the constructions hereinafter set forth, and the scope of the invention will be indicated in the claims.

BRIEF DESCRIPTION OF THE DRAWING

For a fuller understanding of the invention, reference is had to the following description taken in connection with the accompanying drawing, in which:

FIG. 2 is a section taken along the line 2—2 of FIG. 1; and

FIG. 3 is a partial implant section showing a healing cap held in place with a screw.

DESCRIPTION OF PREFERRED EMBODIMENTS

Figure 1:
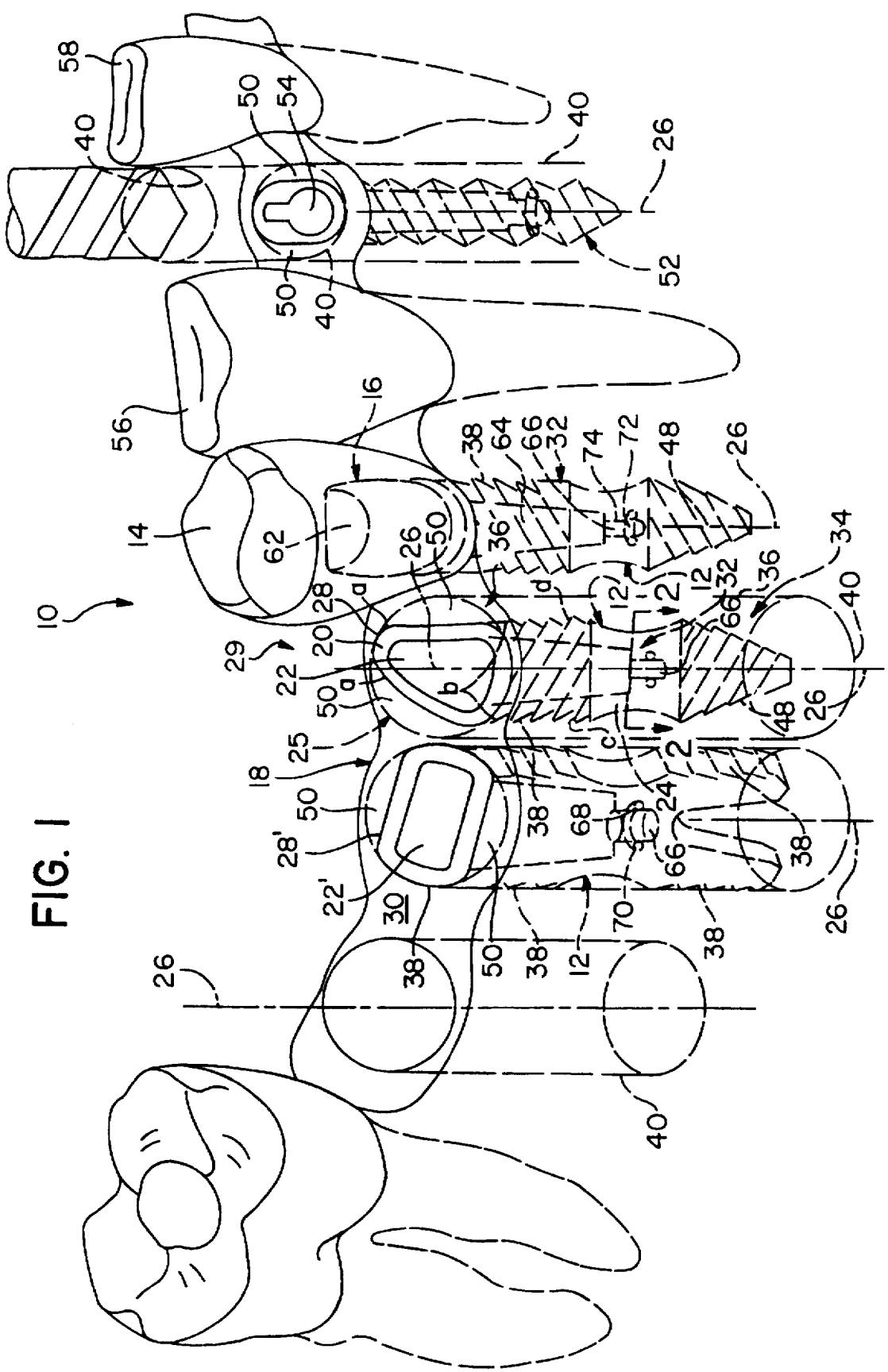
FIG. 1 is a semi-schematic view in perspective of a jawbone having an implant system in accordance with the invention.

With reference to FIG. 1, an implant system 10 in accordance with the invention includes implants 12, artificial crown 14 and an abutment 16 that connects between an implant 12 and the crown 14. As illustrated, and as is known in the art, the implants 12 are imbedded or submerged in the jawbone 18 of a user. It has been proven in the last 25 years, that when an implant 12 is fabricated of titanium, there is a high probability that the titanium will integrate with the bone structure of the jaw 18 to provide a permanent integral assembly.

The following description is stated in the singular but is applicable to both implants 12.

As explained hereinafter, the implant 12 is first installed into the jawbone 18 to a depth that leaves a transverse surface 20 exposed for attachment of the abutment 16 and crown 14. A central opening 22 extends longitudinally into the body 24 of the implant 12, being generally centered about a longitudinal axis 26 of the implant 12. The outer periphery 28 of the body cross section at the proximal end 29 that is close to the gum surface 30 is non-round, in particular, an ovoidal shape is illustrated. (In the adjacent implant 12', the periphery 28' is generally rectangular as is the central opening 22'.) The central opening 22 has an ovoid shape similar to that of the periphery 28 such that the transverse surface 20 is a closed loop strip, somewhat similar in appearance to a race track.

The lateral surface 32 of the implant 12 is of irregular shape. It is not uniformly symmetrical about the longitudinal axis 26, but rather has a configuration corresponding to the shape of the jawbone 18 and the shape of a natural tooth (not shown), which is missing and needs replacement, at the location where the implant 12 is to be used. However, portions of the lateral surface 32 lie on a common imaginary cylindrical surface 36 that is concentric with the axis 26 and represents a maximum radial distance of the implant 12 from the axis 26. These portions of the common cylindrical surface 36 may be formed anywhere along the length of the implant 12 between the proximal end 29 adjacent to the gum surface 30 and the distal end 34 imbedded deeply in the jawbone 18, and these portions include external thread segments 38. For example, between the points a—a on the periphery 28, the implant surface is a threaded part of the circular cylinder 36. Similarly, between the points b—b on the periphery 28, the surface is part of the same cylindrical surface 36. Thus, the threaded portions a—a and b—b of the periphery 28 lie on the surface of the imaginary cylinder 36, whereas the remainder of the periphery 28 between points a and b lies inside the imaginary cylinder 36. Similarly, threaded segments 38 identified at c and d, lie on the same cylindrical surface 36.

It is as though an externally fully threaded cylindrical implant had selected parts of its threaded surface removed, while leaving other selected portions of the threaded surface.

In preparing the jawbone 18 to receive an implant 12, an incision is made at the crest 30 of the gum and the jawbone is exposed, all in a conventional manner as with prior art submergible implants. Then, a cylindrical socket or hole 40 with internal threads (not shown) is drilled into the bone. This threaded cylindrical socket 40 is generally the same diameter as the imaginary cylinder 36. Thus, the threaded segments 38 on the lateral surface 32 of the implant 12 can be screwed with engagement into the internal threads of the hole 40. Thereby, the implant 12 is held in alignment with the longitudinal axis 26 although full threaded contact is not made everywhere in the internally threaded hole 40.

Even though there is not a full surface to surface contact between the implant 12 and the internal threaded surface of the hole 40 in the jawbone 18, the implant 12 does not wobble in the hole 40. When the implant cross section has a two-ended periphery, for example as at the transverse proximal surface 20, there is sufficient engagement to prevent motion of the proximal end except in rotation around the axis 26.

FIG. 2 is a section 2—2 taken through the implant 12 between the proximal and distal ends at a right angle to the axis 26. As the section indicates, there is threaded engagement 38 with the internal hole 40 over more than half of the circumference of that circle. The implant 12 will not wobble in the hole at the cross section. Basically, where the implant body 24 is located asymmetrically with respect to the longitudinal axis 26, the implant will not wobble at that cross section when the ends 42 of the threaded portion 38 are separated by a chordal line 44 that subtends an angle 46 less than 180°.

Clearly, many cross sections can be provided with threaded portions 38 that will prevent wobble of the implant 12 in the hole 40. For example, a generally triangular cross section, or a cross section with four equi-spaced lobes will prevent wobble when the lobes threadably contact the internal threaded surface of the cylindrical hole 40.

The implant 12' that is bifurcated at the distal end is illustrated in FIG. 1. The branches that simulate to a degree the root of an actual tooth, include threaded portions 38, which as in the implant 12, engage the internal threads of the cylindrical threaded hole 40 in the jawbone. The central opening 22 in the implant 12 and its counterpart opening in the other illustrated implants may be oriented with its longer axis parallel to the crest of the jawbone 18, transverse to the crest of the jawbone 18, or at any angle intermediate those two positions, as best suits the position on the jawbone and the shape of the implant that is selected for use.

The implant 12 has a threaded extension 48 that is concentric with the axis 26. The threads are a self-tapping type such that the implant, as it is threaded into the hole 40 in the jawbone and nears its full penetration, will also penetrate the bottom of the hole 40 and make further engagement with the jawbone so as to preclude distal wobbling during the extended period when osseointegration takes place. With such an implant 12, the hole 40 in the jawbone may be made with threads only part way in from the gum crest, or the hole 40 may be shortened. Then the self tapping end 48 of the implant 12 completes the tapping of the hole, making its own threads. The hole 40 may also have a smaller diameter near its bottom then at the gum line, with a stepped or tapered transition between the two diameters, to facilitate self-tapping.

Experiments have proven that the osseointegration process will fill the intentionally formed voids 50 between the implant 12, 12' and the outlines of the internally threaded cylindrical hole 40 with solid bone such that no substantial spaces remain, and the titanium metal becomes integral with the bone structure. Because of this remolding of the bone to the countours of the implant, it is possible when multiple implants are to be positioned adjacent to each other, that the center lines 26 be moved closer together than with prior art implants (not shown), which have fully cylindrical bodies.

For example, in the prior art it is desirable to maintain approximately 0.200 inches between adjacent holes 40 to assure strength in the bone. With the present implant in accordance with the invention, it is possible to bring adjacent holes 40 within approximately 0.080 inches of each other. After the voids 50 between the implant and the hole wall 40 are filled with new-growth material, the strength of the system using the present implant is as at least as good as in the prior art with its wider implant spacing. Thus, a more natural association between implants and the remaining natural teeth can be achieved; the implant can be placed closer to the natural teeth.

The implant 52 is similar to the implants 12 except that the central opening 54 has a key-hole shape. The contours of the central openings in implants in accordance with the invention is not limited to the three shapes that are illustrated and discussed. An essential feature in these implants and in the central openings is that they have a non-round configuration. Thereby, threaded engagement can be made with a circular hole 40 formed in the jawbone to receive an implant, as described, and still provide voids 50 between the implant and the threaded hole 40 at least some of the cross sections between the proximal end near the crest of the jawbone and the distal end imbedded deeply in the jawbone.

The implant 52 is illustrated at a position between two natural teeth 56, 58 where there is barely enough room to drill the hole 40 in the jawbone. In fact, in some instances, it may be necessary to remove portions of the natural teeth 56, 58 to provide sufficient space to drill a hole 40. Nevertheless, although little room is available to drill the hole 40 at installation of the implant, after osseointegration, a substantial web of bone will form in the voids 50 between the implant and the two adjacent natural teeth 56, 58 thereby providing adequate bone strength. Closer spacing of the teeth is achieved and a natural appearance is provided.

The abutment 16 includes a core 62 connected integrally to an elongated post 64. In cross section, the post 64 is shaped to fit within the opening 22, 22' of the implant 12, 12' with a fit between post/implant interfaces that is suitable for cementing the post to the implant in the final stages of construction of the prosthesis. Cements suited to this purpose are well known in the dental arts. The post 64 may taper away from the core 62 or may have surfaces aligned to the axis 26 depending upon the manufacturing methods that are used in preparing the implants and abutments. The central openings in the implants will be longitudinally tapered or parallel (cylindrical) relative to the axis 26 to correspond with the post 64.

The crown 14 is formed in connection with the core 62 by methods and techniques well known in the dental arts. The core may be of many shapes, as are known. Non-round contours of the core 62 provide a greater volume of metal in the facial lingual direction where the greater shearing forces are exerted and prevent rotation or axial separation of the crown 14 relative to the abutment 16. The connections between the crown 14, abutment 16 and implant 12, 12', 52 are effective without use of screws between them.

The cement (not shown) that holds the post 64 in the central opening of the implant is the weakest link in the assembly. Thereby, the cement is the most likely location for failure, if any, under excessive loads. In such an instance, or merely to repair a crown or change a crown, the abutment may be entirely separated from the implant at the cemented interface without damaging the implant. Thus, maintenance or replacement of the prosthesis is easily effected and discomfort to the user is minimized in the procedures. There is no need to remove an implant from the jawbone as the elongated opening 22, 22', 54, is effective in preventing rotation of the abutment relative to the implant. Thus, there is little, if any wear at this interface.

Also, in threading an implant into the jawbone, a tool (not shown), similar to a screw driver, that is preshaped to match the opening 22, 22', 54, as illustrated, or other selected opening shapes, is readily provided. Thereby, there is little danger of slippage between the implant which is being threaded into the jawbone, and the driving tool. Thus, damage to the implant during installation is unlikely. As stated, the longer axis of the implant opening can be oriented in any direction around its center line 26 as suits the location on the jawbone and the shape of the implant.

Although, in the discussions above, the hole or socket 40 formed in the jawbone was described as internally threaded, it should be understood that a smooth bore may also be used. In such an implant installation, the implant may have self tapping threaded portions or the implant may be without external threads. However, a press, friction fit would then be provided between the implant and the socket or hole 40 in the bone instead of the threaded interface that has been indicated above and in the figures. In those embodiments in accordance with the invention where no externally threaded portions are used on the implant and the hole 40 in the bone is not threaded, the implant still presents the non-round cross sections relative to the cross section of the hole 40 such that voids 50 will still be provided wherein bony structure will grow in the process of osseointegration.

Whereas, in the implants of FIG. 1, different and separated portions 38 are illustrated along the length of the respective implants, it should be understood that in alternative embodiments in accordance with the invention the threaded portions may occur continuously from the proximal end substantially to the distal end, however, still not being threaded around a full circumference and thereby providing void spaces 50 wherein bone will grow.

Implants in accordance with the invention can also be formed without the threaded extension 48 at the distal end. Such implants are not illustrated.

In FIG. 1, the central openings 22, 22', 54, include a right cylindrical chamber 66 at the extreme inner end and concentric with the longitudinal axis 26. A groove 68 in the cylindrical wall of the chamber 66 receives a small O-ring 70 that partially protrudes into the chamber 66.

To complement this construction, the post 64 of the abutment 16 is provided with a grove 72 to receive therein the O-ring 70 when the abutment 16 is inserted into the implant. The groove 72 on the abutment 16 is on a small cylindrical extension 74 that is provided at the end of the post 64.

In use, after the cement has been applied and the abutment 16 is inserted into the central opening of the implant, the practitioner gets a feedback, a "feel", that the abutment is properly positioned when the O-ring "snaps" into place in the grove 72 on the abutment 16. Also the O-ring frictionally holds the post before the cement sets.

Abutments in accordance with the invention may also be without this O-ring feature.

Further, the cylindrical wall of the chamber 66 may be threaded on one or both sides longitudinally of the O-ring groove 68. Thereby, during the period when osseointegration takes place, a cover or healing cap 76 may be attached to the implant to cover (FIG. 3) the central opening 22, 22', 54, and also to shape the gum tissues for subsequent attachment of the abutment and crown as is known in the implantation arts. The healing cap or cover 76 is held in place by a screw 78 that passes through the cover 76 and engages the threads 80 on the inner surface on the chamber 66.

Sealing means, e.g. a gasket or cement (not shown), may be used between the implant face and the cover 76. Also, the screw 78 may have an extension 82 (broken lines) having a head 84 suited for driving the screw 78, e.g. a slot or Allen head or Phillips head recess, or a hex shaped perimiter. The sloping shoulder 86 holds the cover 76 in place and the extended body 82 is used in attaching a temporary crown 90 during the healing process.

It will thus be seen that the objects set forth above, and those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

What is claimed is:

1. A dental implant system for connection in the jawbone of a patient, comprising:

an implant having an elongated body, said body having a longitudinal axis and a proximal surface generally transverse to said longitudinal axis, said proximal surface having a non-round peripheral edge as viewed along said axis, and an opening having a non-round cross-section extending from said proximal surface axially into said body, said elongated body having a non-round cross section extending the entire length thereof and having a major axis and a minor axis orthogonally positioned, said non-round cross section being one of ovoid and generally rectangular, and including two opposed first portions on said major axis that are surfaces of a circular cylinder, said first portions being threaded for engagement in a circular hole formed in a jawbone, said non-round cross section also including two opposed substantially continuous non-threaded second portions located between said first portions, said two first portions and said two second portions together defining said non-round cross section of said body, a first distance between said opposed second portions on said minor axis being less than a second distance between said opposed first portions on said major axis, whereby adjacent implants may be placed closer together in said jawbone by having said adjacent implants with second portions opposed.

2. A dental implant system as in claim 1, wherein said non-round cross section of said opening is one of generally rectangular, ovoidal and key-hole shaped.

3. A dental implant system as in claim 1, further comprising a screw tip, extended concentrically with said longitudinal axis at a distal end of said elongated body for self-engagement in said jawbone when said implant as inserted into a prepared jawbone opening, said distal end being stabilized when engaged in said jawbone.

4. A dental implant system as in claim 1, further comprising an abutment having a core at a first end for connection to a prosthetic tooth crown, and a post at a second end for extending into said opening in said implant body, a cross section of said post corresponding in shape to said non-round cross section of said opening, said post when seated in said opening being non-rotatable relative to said body about said longitudinal axis.

5. A dental implant system as in claim 4, further comprising connection means for engaging said abutment with said implant, said connection means releasably engaging said abutment only at an end of said post away from said core.

6. A dental implant system as in claim 1, wherein a distal end of said opening includes a chamber, said chamber having a generally circular cylindrical wall.

7. A dental implant system as in claim 6, wherein said chamber has a groove in said chamber wall, said groove encircling said longitudinal axis, said groove having a depth and a width to cradle an O-ring therein, said depth being less than a cross sectional diameter of said O-ring.

8. A dental implant system as in claim 7, further comprising an abutment having a core at a first end for connection to a prosthetic tooth crown, and a post at a second end for extending into said opening in said implant body, a cross section of said post corresponding in shape to said non-round cross section of said opening, said post when seated in said opening being non-rotatable relative to said implant body about said longitudinal axis.

9. A dental implant system as in claim 8, wherein said post includes a circular cylinder extending from an end away from said core, said cylinder being receivable in said implant chamber when said abutment seats in said implant body, a cylindrical surface of said cylinder having a groove with a depth and width to receive therein an O-ring, said post groove being positionable in opposition to said implant chamber groove when said abutment is seated in said implant.

10. A dental implant system as in claim 9, further comprising an O-ring seated in at least one of said implant chamber groove and said post groove.

11. A dental implant system as in claim 6, further comprising an abutment having a core at a first end for connection to a prosthetic tooth crown, and a post at a second end for extending into said opening in said implant body, a cross section of said post corresponding in shape to said non-round cross section of said opening, said post when seated in said opening being non-rotatable relative to said implant body about said longitudinal axis.

12. A dental implant system as in claim 11, wherein said post includes a circular cylinder extending from an end of said post away from said core, said cylinder being receivable in said implant chamber when said abutment seats in said implant body.

13. A dental implant system as in claim 6, wherein said circular cylindrical wall of said implant chamber is threaded.

14. A dental implant system as in claim 13, further comprising a screw for engaging said threaded chamber wall, and a cover for seating on said proximal surface of said implant and for covering said hole in said proximal surface, said screw extending through said cover and threadably engaging said threaded chamber wall, said cover being tightened on said proximal surface by rotation of said screw in a first direction and released from said proximal surface by rotation of said screw in an opposite second direction.

* * * * *